United States Patent [19]

May

[11] 4,034,473
[45] July 12, 1977

[54] SUTURE CUTTER

[75] Inventor: Edwin A. May, Ridgewood, N.J.

[73] Assignee: International Paper Company, New York, N.Y.

[21] Appl. No.: 643,668

[22] Filed: Dec. 23, 1975

[51] Int. Cl.² ........................................ B26B 17/04
[52] U.S. Cl. ............................... 30/181; 128/305; 128/318
[58] Field of Search ............ 30/179, 124, 186, 188, 30/235, 238, 181; 128/305, 354, 303, 318

[56] References Cited

U.S. PATENT DOCUMENTS

| 2,254,738 | 9/1941 | Gamache | 30/175 |
|---|---|---|---|
| 3,054,182 | 9/1962 | Whitton | 30/179 |
| 3,353,531 | 11/1967 | Armao | 30/235 X |
| 3,576,072 | 4/1971 | Foster | 30/124 |
| 3,651,811 | 3/1972 | Hildebrandt et al. | 128/303.17 |
| 3,659,343 | 5/1972 | Straus | 30/124 |
| 3,672,054 | 6/1972 | Kaufman | 30/294 |

FOREIGN PATENT DOCUMENTS 1,282,243   7/1972   United Kingdom ................. 30/124

Primary Examiner—Robert W. Michell
Assistant Examiner—Michael H. Thaler
Attorney, Agent, or Firm—Finnegan, Henderson, Farabow & Garrett

[57] ABSTRACT

A suture cutter for cutting a suture in a slicing action including a first arm having a free end insertable under a suture and an elongated portion extending at an obtuse angle to the free end, and second arm having a free end and an elongated portion manually movable toward the elongated portion of the first arm, the elongated portions of both arms forming a handle for grasping the suture cutter. A straight edge cutting blade is attached to the free end of the second arm so that the cutting edge of the blade is at an angle to the elongated portion of the second arm ensuring a slicing cutting action on the suture when the suture cutter is operated without a resilient flexing of the second arm.

11 Claims, 9 Drawing Figures

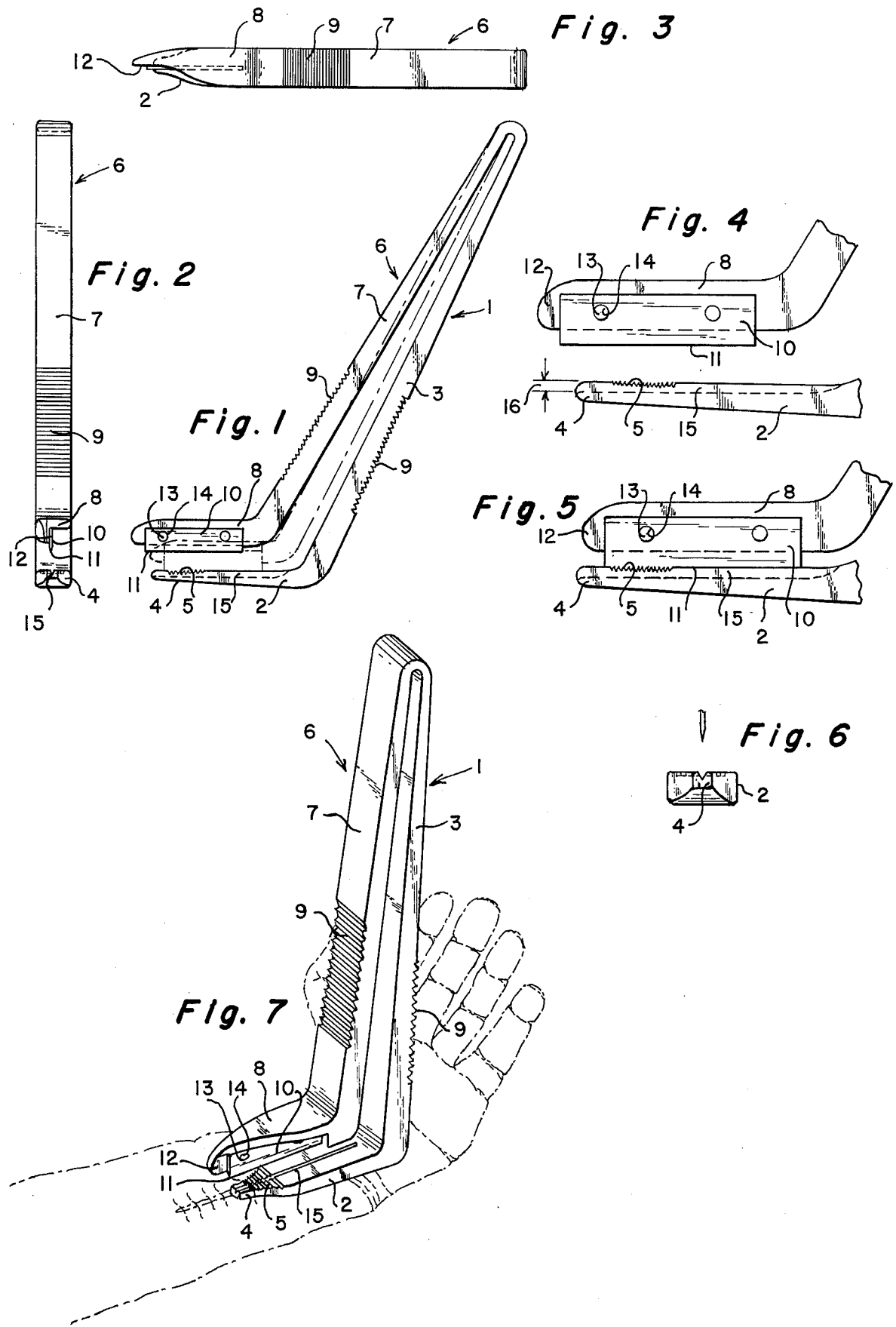

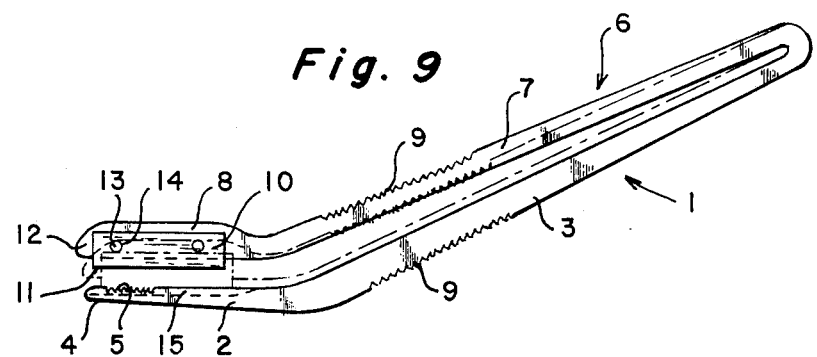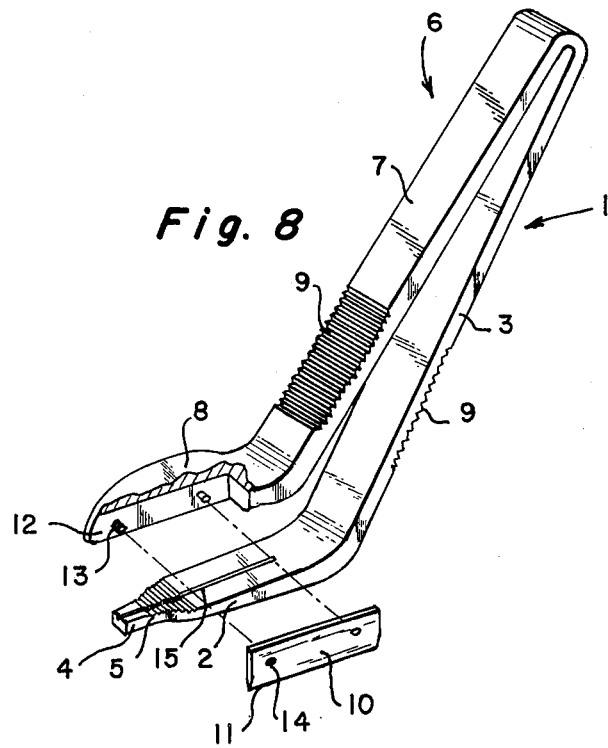

SUTURE CUTTER

The present invention relates to a surgical instrument for cutting a suture and, more particularly, to a surgical instrument for cutting a suture in a slicing action.

Many of the conventional suture cutters are unsatisfactory because the suture to be severed is cut in a chopping or wedging action. This frequently causes an undesirable frayed or incomplete cutting of the suture. A more desirable suture cutting is achieved by a slicing action. However, those conventional suture cutters which are shown to cut a suture in a slicing action also are unsatisfactory because they do not firmly hold the suture in position during the cutting operation, require awkward or excessive amount of manual manipulation by the operator, or cause excessive tugging and lifting of the suture from the skin. Some suture cutters even have exposed cutting blades which are the frequent cause of accidental skin punctures. Others mandate overly sophisticated structures to achieve a suitable cutting action.

Finally, many of the conventional suture cutters are not made of molded resilient materials or the like which are relatively inexpensive to manufacture and disposable after a single use. Those conventional suture cutter which are disposable usually do not provide an accurate cutting action on the suture and produce the same unsatisfactory results described above.

In view of the deficiencies of the conventional suture cutters, it is an object of this invention to provide an improved suture cutter for cutting a suture in a slicing action.

Another object of this invention is to provide a suture cutter which is quickly and easily operated with minimum manual manipulation.

Another object of this invention is to provide a suture cutter which cuts the suture close to the skin surface.

Another object of this invention is to provide a suture cutter which ensures an accurate cutting of the suture.

A further object of this invention is to provide a suture cutter which requires a minimum of lifting of the suture from the skin.

Still another object of this invention is to provide a suture cutter having its cutting blase protected for preventing accidental skin puncture.

Finally, an object of this inention is to provide a relatively inexpensive and disposable suture cutter which achieves the above-described objects.

Additional objects and advantages of the invention will be set forth in part in the description which follows, and in part will be obvious from the description, or may be learned by practice of the invention. The objects and advantages of the invention may be realized and attained by means of the instrumentalities and combination particularly pointed out in the appended claims.

To achieve the foregoing objects and in accordance witn the purpose of the invention, as embodidied and broadly described herein, the suture cutter of the invention comprises; (1) a first arm having a first free end for insertion under a suture and an elongated portion extending at a first obtuse angle to the first free end; (2) a second arm having an elongated portion manually movable toward the elongated portion of the first arm, the second arm being connected to the elongated portion of the first arm, the elongated portions forming a handle for grasping the suture cutter, the second arm terminating in a second free end; and (3) cutter means on the second free end, the cutter means including a straight edge blade portion aligned at an angle to the elongated portion of the second arm, the angular relationship of the straight edge blade portion and the elongated portion of the second arm ensuring a slicing action of a suture held by the first arm even in the absence of resilient flexing of the second arm as the second arm is moved towards the first arm.

Preferably, the suture cutter described above has the straight edge blade portion of the cutter means aligned at a second obtuse angle with the elongated portion of the second arm, the first obtuse angle being substantially equal to the second obtuse angle and slightly greater than 90°.

It is also preferred that the suture cutter have the first free end with a thin and tapered terminal portion for positioning the suture thereon. Preferably, the suture cutter also incluses suture-retaining means on the interior surface of the first free end and at least one groove for guiding the cutting means, the groove extending longitudinally and intersecting the suture-retaining means.

It is preferred that the suture cutter previously described have the first and second arms formed of a single piece of molded resilient material and that the suture cutter be disposable.

The invention consists in the novel parts, constructions, arrangements, combinations and improvements shown and described. The accompanying drawings, which are incorporated in and constitute a part of this specification, illustrate an embodiment of the invention, and, together with the description. serve to explain the principles of the invention.

OF THE DRAWINGS

FIG. 1 is a side view of the suture cutter in accordance with the teachings of this invention;

FIG. 2 is a front view of the suture cutter of FIG. 1;

FIG. 3 is a top view of the suture cutter of FIG. 1;

FIG. 4 is an enlarged side view of the free ends of the suture cutter of FIG. 1 in an opened position;

FIG. 5 is an enlarged side view of the suture cutter of FIG. 1 in a closed position;

FIG. 6 is an end view of the suture cutter of FIG. 4;

FIG. 7 is a perspective view of the suture cutter if FIG. 1 having a free end inserted under a suture for cutting;

FIG. 8 is a perspective view of the suture cutter of FIG. 7 in an as-molded, preassembled condition; and FIG. 9 is a side view of the suture cutter of FIG. 1 modified to have a greater obtuse angle between the elongated portions and free ends of the arms.

Reference will now be made in detail to the present preferred embodiment of the invention, examples of which are illustrated in the accompanying drawings.

As best seen in FIGS. 1 and 7, the suture cutter, in accordance with the invention, comprises a first arm 1 having a first free end 2 for insertion under a suture and an elongated portion 3 extending at a first obtuse angle to first free end 2. Preferably, first free end 2 has a thin, tapered, terminal portion 4. The configuration of terminal portion 4 provides for an easy insertion of first end end 2 under the suture to be cut and for positioning the suture on first free end 2 which permits cutting the suture close to the skin surface without excessively lifting or tugging the suture.

To ensure that the suture to be cut is firmly positioned on free end 2, it is preferred that suture-retaining means to provided on the interior surface of first free end 2 for retaining the suture thereon during the cutting operation. As herein embodied, the suture-retaining means comprises a plurality of ridges 5 extending transversely across the interior surface of first end 2. These ridges 5 can be locayed adjacent to or on terminal portion 4 to thus allow positioning of the suture cutter thereon with a minimal amount of lifting and tugging of the suture.

In accordance with the invention, the suture cutter further comprises a second arm 6 connected to elongated portion 3 of first arm 1 and having an elongated portion 7 manually movable toward elongated portion 3 of first arm 1. The elongated portions 3 and 7 of arms 1 and 6, respectively, form a handle for grasping the suture cutter. Second arm 6 terminates in a second free end 8. Preferably, elongated portion 7 of second arm 6 is aligned with elongated portion 3 of first arm 1 in a small acute angular relationship. This facillitates the formation of a handle for grasping which requires less manual manipulation and enhances an easier and quicker operation when elongated portion 7 of second arm 6 is manually moved toward elongated portion 3 of first arm 1. It is also preferred that finger grips, such as roughened areas 9, be located on the exterior surface of elongated portions 3 and 7 of arms 1 and 6, respectively, to provide an easier and firmer grasping of the handle.

As herein embodied, the first and second arms of the cutter can be formed of a single piece of molded resilient material and the suture cutter disposable after a single use. As best seen in FIG. 8, the molded arms 1 and 6 are shown formed integrally together and having a resiliency to effect a biasing of arms 1 and 6 toward an open position.

In accordance with the invention, the suture cutter further comprises a cutter means 10, preferably a metal cutting blade, on second free end 8. Cutter means 10 has a straight edge blade portion 11 aligned at an angle to elongated portion 7 of second arm 6 for ensuring a slicing action on the suture held on first free end 2. This angular relationship between the straight edge blade portion 11 and elongated portion 7 eliminates the need for a convex cutting blade and ensures the slicing action even in the absence of any resilient flexing of second arm 6 when second arm 6 is manually moved toward first arm 1. The use of the straight edge cutting blade reduces the chance of an accidental skin puncture and makes the suture cutter less costly and easier to manufacture.

As best seen in FIG. 8, to facilitate attachment of cutting blade 10, it is preferred that second free end 8 have a planar surface 12 integrally formed and projecting downwardly from the interior surface of second free end 8 toward first free end 2. As herein embodied, planar surface 12 has at least one integrally molded boss 13 and cutting blade 10 has at least one hole 14 compatible with boss 13. For assembling cutting blade 10 to planar surface 12, boss 13 extends through hole 14 for mounting blade 10 and the end of boss 13 is subsequently hot-headed or ultrasonically upset to secure blade 10 thereon. Planar surface 12 is formed so as to prevent an exposed cutting blade.

Referring again to FIGS. 1 and 7, as here embodied, straight edge blade portion 11 of cutting blade 10 is aligned at a second obtuse angle with elongated portion 7 of second arm 6 with the first obtuse angle between first free end 2 and elongated portion 3 of first arm 1 and the second obtuse angle being substantially equal. As best seen in FIG. 1, it is preferred that the first and second obtuse angles be slightly greater than 90° to provide the maximum degree of slicing action rearwardly and longitudinally along first free end 2 when elongated portion 7 of second arm 6 is pressed toward elongated portion 3 of first arm 1.

However, in accordance with the invention, the degree of slicing action can be made conveniently dependent upon the angular relationship between straight edge blade portion 11 and elongated portion 7 of second arm 6. As best seen in FIG. 9, a lesser degree of slicing action occurs when the first and second obtuse angles are increased or are greater than those shown in FIG. 1

To further simplify the structural configuration of the suture cutter, it is preferred that second free and end 8 be aligned substantially parallel to first end 4 and cutting blade 10 be mounted on second free end 8 so that straight edge blade portion 11 is aligned parallel to second free end 8.

To ensure an accurate and proper slicing action on the suture, it is herein embodied that at least one groove 15 be formed on the interior surface of first free end 8 for guiding cutting blade 10 during the cutting operation and which extends longitudinally and intersects the plurality of ridges 5. Preferably, and as best seen in FIG. 4, groove 15 has a depth 16 equal to or greater than the depth of the ridges 5 so that cutting blade 10 completely and cleanly slices through a suture positioned between a pair of ridges 5. It should be noted that the groove 15 need only be of a sufficient width to guide the thin straight edge blade portion 10 through ridges 5. Consequently, the first free end 2 can be tapered significantly to a thickness and width just sufficient to carry groove 15 and ridges 5. This ensures easy insertion, proximity to the skin surface, and minimizes tugging and lifting of the suture.

To operate the preferred embodiment of the suture cutter, the operator grasps the handle of the suture cutter formed by elongated portions 3 and 7 of arms 1 and 6, respectively. Normally, the thumb is positioned on the roughened area 9 on elongated portion 7 of second arm 6 while the forefingers are positioned on the roughened area 9 on elongated portion 3 of first arm 1. As best shown in FIG. 4, before elongated portion 7 of second arm 6 is manually moved toward elongated portion 3 of first arm 1, the cutting blade 10 is in an inoperative position above first free end 2.

The thin, tapered, terminal portion 4 of first free end 2 is then inserted under a suture for positioning the suture on the ridges 5 of first free end 2. Due to the configuration of first free end 2, insertion under and positioning of the suture is done close to the skin with a minimum amount of tugging and lifting of the suture.

When the suture is properly positioned on ridges 5, the suture cutter is operated for severing the suture by manually moving elongated portion 7 of second arm 6 toward elongated portion 3 of first arm 1. When this is done, straight edge blade portion 11 of cutting blade 10 is brought downwardly in a rearward and longitudinal direction as shown in FIGS. 1 and 4. Due to the angular relationship of straight edge blade portion 11 and elongated portion 7, the suture positioned on ridges 5 is cut in a slicing action. This slicing action is accomplished even in the absence of any resilient flexing of second arm 6.

As straight edge blade portion 11 of cutting blade 10 is moved across the suture, the cutting blade 10 is guided into a closes position by groove 15 to ensure that the suture is accurately, cleanly, and completely sliced by straight edge blade portion 11. This is best shown in FIG. 5.

It will be apparent to those skilled in the art that various modifications and variations could be made in the suture cutter of the invention without departing from the scope or spirit of the invention.

What is claimed is:

1. A suture cutter for slicing a suture comprising:
   a. a first arm having a first free with a substantially planar surface for insertion under a suture and an elongated portion extending at a first obtuse angle to said first free end;
   b. a second arm having an elongated portion manually movable from a first position toward the elongated portion of said first arm into a second suture cut position, said second arm being connected to the elongated portion of said first arm, said elongated portions forming a handle for grasping said suture cutter, said second arm terminating in a second free end; and
   c. cutter means on said second free end, said cutter means including a straight edge blase portion aligned at an angle to the elongated portion of said second arm and lying generally parallel to the planar surface of said first free end when the elongated portion of said second arm lies in said first position, the angular relationship of said straight edge blade portion and the elongated portion of said second arm and the planar surface of said first free end being such that said straight edge blade portion lies generally parallel to the planar surface of said first free end when the elongated portion of said second arm is moved into its second suture cut position thereby ensuring a slicing action to a suture held by said first arm in a direction substantially parallel to the planar surface of said first free end even in the absence of resilient flexing of said second arm as the elongated portion of said second arm is moved from its first position toward said first arm into its second position.

2. The suture cutter of claim 1 wherein said straight edge blade portion is aligned at a second obtuse angle with the elongated portion of said second arm, said first obtuse angle being substantially equal to said second obtuse angle.

3. The suture cutter of claim 2 in which said first and second obtuse angles are slight greater than 90° for providing the maximum slicing motiion substantially longitudinally along the planar surface of said first free end when the elongated portion of said second arm is pressed toward the elongated portion of said first arm.

4. The suture cutter of claim 1 wherein the elongated portion of said second arm is aligned with the elongated portion of said first arm in a small acute angular relationship.

5. The suture cutter of claim wherein said cutter means includes a metal blade carried by said second free end.

6. The suture cutter of claim 1 wherein said first free end has a thin, tapered, terminal portion for facilitating easy insertion of said first free end under the suture and positioning of the suture on said first free end.

7. The suture cutter of claim 1 wherein said first and second arms are formed of a single piece of molded resilient material.

8. The suture cutter of claim 7 including means on the planar surface of said first free end for retaining a suture thereon, said planar surface carrying at least one groove for guiding said cutting means, said groove extending longitudinally and intersecting said suture retaining means.

9. The suture cutter of claim 8 wherein said suture-retaining means comprises a plurality of ridges extending transversely of the planar surface of said first free end, having a depth equal to or greater than the depth of said ridges to enable the cutting edge of said cutting blade to completely and cleanly slice throuch a suture seated between a pair of ridges during operation of said suture cutter.

10. The suture cutter of claim 8 wherein said second free end has a planar surface with at least one integrally molded boss thereon, said cutting blade having a hole compatible with said boss, said boss extending through said hole for mounting said blade on said boss.

11. The suture cutter of claim 10 including finger grips located on the exterior surface of the elongated portions of said arms for providing easier and firmer grasping of the handle operation of said suture cutter.

* * * * *

UNITED STATES PATENT AND TRADEMARK OFFICE
CERTIFICATE OF CORRECTION

PATENT NO. : 4,034,473
DATED : July 12, 1977
INVENTOR(S) : EDWIN A. MAY

It is certified that error appears in the above-identified patent and that said Letters Patent are hereby corrected as shown below:

Column 5, claim 1, line 13, after "free" insert --end--.

Column 5, claim 1, line 26, change "blase" to --blade--.

Column 6, claim 3, line 4, change "slight" to --slightly--.

Column 6, claim 3, line 5, change "motiion" to --motion--.

Column 6, claim 5, line 13, after "claim" insert --1--.

Column 6, claim 9, line 32, after "end," insert --said groove--.

Column 6, claim 9, line 34, change "throuch" to --through--.

Signed and Sealed this

Fourth Day of October 1977

[SEAL]

Attest:

RUTH C. MASON
Attesting Officer

LUTRELLE F. PARKER
Acting Commissioner of Patents and Trademarks